United States Patent [19]
Duzick et al.

[11] Patent Number: 6,127,585
[45] Date of Patent: Oct. 3, 2000

[54] CATALYSTS FOR HALOGENATED HYDROCARBON PROCESSING, THEIR PRECURSORS AND THEIR PREPARATION AND USE

[75] Inventors: Timothy C. Duzick, Hockessin; Velliyur Nott Mallikarjuna Rao, Wilmington, both of Del.; Munirpallam A. Subramanian, Kennett Square, Pa.

[73] Assignee: E. I. du Pont de Nemours and Company, Wilmington, Del.

[21] Appl. No.: 09/077,267
[22] PCT Filed: Nov. 26, 1996
[86] PCT No.: PCT/US96/18967
§ 371 Date: May 27, 1998
§ 102(e) Date: May 27, 1998
[87] PCT Pub. No.: WO97/19751
PCT Pub. Date: Jun. 5, 1997

Related U.S. Application Data

[60] Provisional application No. 60/007,734, Nov. 29, 1995.
[51] Int. Cl.$^7$ .......................... C07C 19/08; C07C 21/18; B01T 27/138; B01T 27/132
[52] U.S. Cl. .......................... 570/124; 502/226; 502/228; 502/181
[58] Field of Search ........................... 570/124; 502/181, 502/330, 226, 228

[56] References Cited

U.S. PATENT DOCUMENTS

| | | | |
|---|---|---|---|
| 2,379,697 | 7/1945 | Evans et al. | 260/680 |
| 2,823,235 | 2/1958 | Penrose et al. | 260/580 |
| 3,265,636 | 8/1966 | Spiegler | 252/447 |
| 3,271,327 | 9/1966 | NcEvoy et al. | 252/472 |
| 4,760,187 | 7/1988 | Kosak | 564/417 |
| 4,929,781 | 5/1990 | James, Jr. et al. | 585/310 |
| 4,980,324 | 12/1990 | Kellner et al. | 502/36 |
| 5,057,470 | 10/1991 | Kellner | 502/35 |
| 5,094,988 | 3/1992 | Kellner et al. | 502/181 |
| 5,202,510 | 4/1993 | Kellner | 570/176 |
| 5,276,240 | 1/1994 | Timmons et al. | 585/642 |
| 5,315,048 | 5/1994 | Van Der Puy et al. | 570/176 |
| 5,430,214 | 7/1995 | Smith et al. | 585/641 |
| 5,447,896 | 9/1995 | Rao | 502/184 |
| 5,559,069 | 9/1996 | Rao et al. | 502/226 |
| 5,561,096 | 10/1996 | Schoebrechts et al. | 502/330 |
| 5,629,462 | 5/1997 | Rao | 570/176 |
| 5,847,242 | 12/1998 | Rao et al. | 570/151 |

FOREIGN PATENT DOCUMENTS

| | | | |
|---|---|---|---|
| 0 331 991 A2 | 9/1989 | European Pat. Off. | C07C 19/08 |
| 0 516 000 A1 | 12/1992 | European Pat. Off. | C07C 17/20 |
| WO 95/05353 | 2/1995 | WIPO | C07C 19/08 |

OTHER PUBLICATIONS

D.–H. Menz and B. Ehrhardt, Study of the Thermal Behavior of [Cr(NH3)6]MF6(M=Cr, Al, Fe, Ga and In) and [Cr(NH3)6]F3.HF.H2O, *Journal of Thermal Analysis*, 42, 925–935, 1994.

Wieghardt unde Hans Siebert, Schwingungsspektren und Kristallgitter, *Journal of Molecular Structure*, 7, 305–313, 1971.

L.E. Manzer and V.N.M. Rao, Catalytic Synthesis of Chlorofluorocarbon Alternatives, *Advances in Catalysis*, 39, 329–350, 1993.

*Primary Examiner*—David W. Wu
*Assistant Examiner*—Tanya Zalukaeva

[57] ABSTRACT

Processes are disclosed for decreasing the chlorine to carbon ratio for halogenated hydrocarbons containing chlorine and from 1 to 6 carbon atoms, in the presence of a multiphase catalyst. The processes each involve (1) preparing a single phase solid catalyst precursor which has a structure that collapses at a temperature of about 400° C. or less and has the formula $(NH_3)_6Ru_{1-r-s}Co_rCr_sMF_6$, where r+s is in the range of 0.00 to 0.99, and M is at least one trivalent metal selected from the group consisting of Al, Cr, Fe, V, Sc and Ga; and (2) producing the multiphase catalyst by heating the single phase solid catalyst precursor to about 400° C. or less in an non-oxidizing atomsphere to produce a multiphase composition wherein a phase containing ruthenium is homogeneously dispersed with a phase containing metal fluoride.

Also disclosed are single phase fluoride compositions having the formula $(NH_3)_6Ru_{1-r-s}Co_rCr_sMF_6$, where r+s is in the range of 0.00 to 0.99, and M is at least one trivalent element selected from the group consisting of Al, Cr, Fe, V, Sc and Ga; and multiphase catalyst compositions consisting essentially of metallic ruthenium and fluorides of at least one element selected from the group consisting of Al, Co, Cr, Fe, V, Sc and Ga, wherein the ruthenium is homogeneously dispersed with phases of the fluorides.

20 Claims, No Drawings

CATALYSTS FOR HALOGENATED HYDROCARBON PROCESSING, THEIR PRECURSORS AND THEIR PREPARATION AND USE

This application represents a national filing under 35 USC 371 of International Application No. PCT/US96/18967 filed Nov. 26, 1996, and claims priority of U.S. Provisional Application No. 60/007,734 filed Nov. 29, 1995.

FIELD OF THE INVENTION

This invention relates to fluoride compositions and their preparation and use, and more particularly to ruthenium and selected metal fluoride catalysts, precursors for such catalysts, and preparation and use of such catalysts for processing halogenated hydrocarbons.

BACKGROUND

A variety of metal catalysts have been proposed for use in processes for dimerizing chlorine-containing fluorocarbons, for dehalogenating halogenated fluorocarbons, for hydrofluorinating halogenated hydrocarbons and for hydrodehalogenating halogenated fluorocarbons (see e.g., PCT Publication No. WO 95/05353 for dimerization examples and L. E. Manzer et al., Adv. Catal. (39) pp. 329–350 (1993) for examples of the other listed processes). The catalysts proposed include catalysts involving combinations of cations. Typically these materials are prepared by depositing a soluble salt of the metal on a support, e.g., silica, alumina and carbon. While this method does provide a combination catalyst, the support material and the material deposited thereon are not uniformly dispersed. Techniques such as coprecipitation which rely upon physical characteristics of individual components (e.g., solubility) also typically yield non-homogeneously dispersed products due to differences in physical and chemical properties of the components. There is an interest in developing means for more homogeneous dispersion of components of multiple cation catalysts which can be used for dimerizing, dehalogenating, hydrofluorinating and hydrodehalogenating halogenated hydrocarbons.

SUMMARY OF THE INVENTION

This invention provides processes for decreasing the chlorine to carbon ratio for halogenated hydrocarbons containing chlorine and from 1 to 6 carbon atoms, in the presence of a multiphase catalyst. The processes are each characterized by (1) preparing a single phase solid catalyst precursor which has a structure that collapses at a temperature of about 400° C. or less and has the formula $(NH_3)_6Ru_{1-r-s}Co_rCr_sMF_6$, where r+s is in the range of 0.00 to 0.99, and M is at least one trivalent metal selected from the group consisting of Al, Cr, Fe, V, Sc and Ga; and (2) producing said multiphase catalyst by heating said single phase solid catalyst precursor to about 400° C. or less in a non-oxidizing atmosphere to produce a multiphase composition wherein a phase containing ruthenium is homogeneously dispersed with a phase containing metal fluoride.

This invention further provides single phase fluoride compositions of the formula $(NH_3)_6Ru_{1-r-s}Co_rCr_sMF_6$, where r+s is in the range of 0.00 to 0.99, and M is at least one trivalent element selected from the group consisting of Al, Cr, Fe, V, Sc and Ga. This invention also provides multiphase catalyst compositions consisting essentially of metallic ruthenium and fluorides of at least one element selected from the group consisting of Al, Co, Cr, Fe, V, Sc and Ga, wherein said ruthenium is homogeneously dispersed with phases of said fluorides.

DETAILED DESCRIPTION

The catalytic processes of this invention include processes for dimerizing, processes for dehalogenating, processes for hydrofluorinating and processes for hydrodehalogenating chlorinated fluorocarbons (i.e., compounds containing only carbon, chlorine and fluorine) and chlorinated hydrofluorocarbons (i.e., compounds containing only carbon, hydrogen, chlorine and fluorine). The chlorinated fluorocarbons and chlorinated hydrofluorocarbons can contain from 1 to 6 carbon atoms. The processes employ a multiphase catalyst prepared in a manner which provides a homogeneous dispersion of ruthenium metal. In accordance with this invention, the catalyst may be made by preparing a decomposable single phase solid catalyst precursor and then converting the precursor to a multiple phase catalyst containing fluorine. In this multiple phase catalyst all the metals other than ruthenium consist essentially of the metal fluorides. A single phase catalyst precursor of the formula $(NH_3)_6Ru_{1-r-s}Co_rCr_sF_6$ may be prepared from aqueous solutions of hexaamine ruthenium trichloride $(NH_3)_6RuCl_3$, $(NH_3)_6CoCl_3$, $(NH_3)_6CrCl_3$, and trivalent metal chlorides, $MCl_3$, selected from the group of consisting of $AlCl_3$, $CoCl_3$, $CrCl_3$, $FeCl_3$, $VCl_3$, $GaCl_3$ and $ScCl_3$, taken in the stoichiometric ratios, Ru:Co:Cr:M=(1-r-s):r:s:1, where r+s is in the range of 0.00 to 0.99 (preferably from 0.10 to 0.90, and more preferably from 0.20 to 0.80) by direct precipitation using aqueous HF (e.g., 48% HF) as the precipitant. The single phase catalyst precursor can also be prepared by dissolving the metal oxides, $M_2O_3$ (i.e., $Al_2O_3$, $Co_2O_3$, $Cr_2O_3$, $Fe_2O_3$, $V_2O_3$, $Ga_2O_3$ or $SC_2O_3$) in aqueous HF (e.g., 48% HF), combining the metal solutions with $(NH_3)_6RuCl_3$, $(NH_3)_6CoCl_3$ or $(NH_3)_6CrCl_3$ taken in the stoichiometric ratios, Ru:Co:Cr:M=(1-r-s):r:s: 1, and employing direct precipitation using the aqueous HF as a precipitant. The recovered solid can be dried at about 110° C. for about 12 hours. Powder X-ray diffraction patterns of catalyst precursors show the formation of single phase products and can be indexed on the basis of a cubic unit cell (space group: Pa3). Infrared and Raman spectra of the catalyst precursors show the presence of hexaammine groups. The microprobe analysis of the catalyst precursors show the Ru:Co:Cr:M:F ratio to be (1-r-s):r:s:1:6. As noted above r+s is in the range of 0.00 to 0.99. Included are embodiments where r is 0.00 and s is up to 0.99, and embodiments where s is 0.00 and r is up to 0.99. Of note for high chromium content are embodiments where r is 0.00 and M is Cr.

It will be evident that providing single phase catalyst precursors as described arranges the components in a structured arrangement where Ru and the other metal components are closely connected through the $NH_3$ and/or F components. In any case, as a result of the arrangement of the components in the precursor, when the single phase structure collapses upon heating, uniformly interspersed phases of ruthenium and metal fluorides are formed. These are referred to herein as "homogeneously dispersed" phases.

It is desirable to convert the single phase precursor to a homogeneously dispersed multiphase composition at a moderately elevated temperature of about 400° C. or less, preferably about 300° C. to 400° C. Conversion to the homogeneously dispersed multiphase composition is conducted in a non-oxidizing atmosphere. By non-oxidizing atmosphere is meant an atmosphere where the ruthenium metal formed by decomposition of the precursor is not oxidized. This multiphase composition can be used as a catalyst for dimerizing, dehalogenating, hydrofluorinating and hydrodehalogenating halogenated hydrocarbons containing chlorine and from 1 to 6 carbon atoms. Preferred uses include use as a catalyst for dimerizing and dehalogenating.

Included in this invention is a process for dimerizing saturated compounds having the formula $C_nH_aCl_bF_c$ where n is an integer from 1 to 4, a is an integer from 0 to 1, b is an integer from 2 to 9, c is an integer from 0 to 9, where a+b+c equals 2n+2, and where two chlorines that are removed are on the same carbon atom, by reacting said compound with hydrogen in the vapor phase to produce olefins of the formula $C_{2n}H_{2a}Cl_{2b-4}F_{2c}$; a process for dehalogenating a saturated compound having the formula $C_mH_dCl_eF_f$ where m is an integer from 2 to 6, d is an integer from 0 to 2, e is an integer from 2 to 4, f is an integer from 3 to 12, where d+e+f equals 2m+2, by reacting said compound with hydrogen in the vapor phase to produce olefins of the formula $C_mH_dCl_{e-y}F_{f-y}$, where y is an integer from 1 to 2 when m is an integer from 2 to 3, and y is an integer from 2 to 4 when m is an integer from 4 to 6, provided that a chlorine atom on each of two adjacent carbons or a fluorine and a chlorine atom on two adjacent carbons, but not a fluorine atom on each of two adjacent carbons are removed; a process for increasing the fluorine content of a saturated or olefinic compound having the formula $C_jH_gCl_hF_i$ where j is an integer from 1 to 6, g is an integer from 0 to 4, h is an integer from 1 to 13, i is an integer from 0 to 13, provided that h is at least 1 when the compound is saturated, by reacting said compound with HF in the vapor phase; and a process for the hydrodechlorination of suitable cyclic and acyclic compounds having the formula $C_kH_pCl_qF_t$ where k is an integer from 1 to 6, p is an integer from 0 to 12, q and t are integers from 1 to 13, where p+q+t equals 2k+2, when the compound is saturated and acyclic, equals 2k when the compound is saturated and cyclic or is olefinic and acyclic, and equals 2k-2 when the compound is olefinic and cyclic, by reacting said compound with hydrogen in the vapor phase.

Homogeneously dispersed multiphase catalysts of ruthenium and fluorides of at least one element selected from the group consisting of Al, Co, Cr, Fe, V, Sc and Ga may be used in accordance with this invention in a process for dimerizing saturated compounds having the formula $C_nH_aCl_bF_c$, by contacting the saturated compounds with the homogeneously dispersed multiphase catalysts in the presence of hydrogen in the vapor phase. Suitable catalysts for this reaction include compositions consisting essentially of fluorides of at least one element selected from the above disclosed group homogeneously dispersed with ruthenium.

The reaction of said compounds of the formula $C_nH_aCl_bF_c$ with hydrogen is conducted in the presence of the catalysts of the instant invention. Typically the reaction is conducted at a temperature from about 100° C. to 400° C., preferably from about 125° C. to 375° C. and more preferably from about 150° C. to about 300° C. Typically, the contact time is from about 1 to about 100 seconds, preferably from about 5 to about 60 seconds. The mole ratio of hydrogen to $C_nH_aCl_bF_c$ compound(s) ordinarily should be at least about 0.25:1. Typically, the molar ratio of hydrogen to said compounds of the formula $C_nH_aCl_bF_c$ ranges from about 0.5:1 to about 10:1, and is preferably from about 0.5:1 to 5:1, and more preferably from about 0.5:1 to 2:1. In general, with a given catalyst composition, the higher the temperature and the longer the contact time, the greater is the conversion to dimerized products. The above variables can be balanced, one against the other, so that the formation of dimerized products is maximized.

Examples of halogenated hydrocarbons of the formula $C_nH_aCl_bF_c$ which may be reacted with hydrogen include, $CCl_4$, $CCl_3CClF_2$, $CCl_3CF_3$, $CF_3CCl_2CF_3$, $CCl_3CF_2CF_3$, $CCl_3CF_2CF_2CF_3$ and $CF_3CCl_2CF_2CF_3$. Of note is a catalytic process for producing cis and trans 2,3-dichloro-1,1,1,4,4,4-hexafluorobutene-2 (i.e., F1316mxx or $CF_3CCl=CClCF_3$) by the reaction of hydrogen with $CCl_3CF_3$. This dimerization reaction is done in the presence of the catalysts of the instant invention and is preferably conducted at a temperature of from about 125° C. to 300° C., more preferably from about 150° C. to 250° C.

Also of note is a catalytic process for producing cis and trans 3,4dichloro-1,1,1,2,2,5,5,6,6,6-decafluorohexene-3 (i.e., F151-10mcxx or $C_2F_5CCl=CClC_2F_5$). Starting materials include 1,1,1-trichloro-2,2,3,3,3-pentafluoropropane. A catalytic process for producing 2,3-trifluoromethyl-1,1,1,4,4-hexafluorbutene-2 (i.e., F151-12mmtt or $(CF_3)_2C=C(CF_3)_2$ from 2,2-dichloro-1,1,1,3,3,3-hexafluoropropane is also of note.

The dimerized products which are unsaturated and/or contain chlorine can be further reacted with hydrogen or a fluorinating agent (e.g., HF) in the presence of the same or optionally a second catalyst. Further reacting the dimerized products with hydrogen (optionally using a second catalyst) can produce hydrofluorocarbons. Reaction with a fluorinating agent can produce a hydrofluorocarbon or a perfluorinated alkane, depending on the fluorinating agent.

The catalyst used for the hydrogenation reaction may be the same catalyst used for the dimerization reaction or may be selected from metals known to provide significant hydrogenolysis activity on supports such as alumina, fluorided alumina and carbon. A preferred catalyst contains at least one metal selected from the group consisting of rhenium, cobalt, nickel, ruthenium, rhodium, palladium, osmium, iridium and platinum supported on carbon with an ash content of less than 0.5% by weight. The reaction of the dimerized products and hydrogen can be performed in liquid or vapor-phase using well-known chemical engineering practice, which includes continuous, semi-continuous or batch operations. The hydrogenolysis process is achieved at atmospheric or superatmospheric pressures.

The fluorinating agent may be chosen from the group consisting of hydrogen fluoride, cobalt fluoride, elemental fluorine or fluoride salts. Any of the known art catalysts and conditions may be used for the hydrofluorination in either the vapor phase (e.g., chromium oxide) or the liquid phase (e.g., an antimony halide).

Homogeneously dispersed multiphase catalysts of ruthenium and fluorides of at least one element selected from the group consisting of Al, Co, Cr, Fe, V, Sc and Ga may be used in accordance with this invention in a process for dehalogenating saturated compounds having the formula $C_mH_dCl_eF_f$, by contacting the saturated compounds with the homogeneously dispersed multiphase catalysts in the presence of hydrogen in the vapor phase. Suitable catalysts for this reaction include compositions consisting essentially of fluorides of at least one element selected from the above disclosed group homogeneously dispersed with ruthenium.

The reaction of said compounds of the formula $C_mH_dCl_eF_f$ with hydrogen is conducted in the presence of the catalysts of the instant invention. Typically the reaction is conducted at a temperature from about 100° C. to 350° C., preferably from about 125° C. to 325° C., and more preferably from about 150° C. to about 275° C. Typically the contact time is from about 1 to about 100 seconds, preferably from about 5 to about 60 seconds. The molar ratio of hydrogen to $C_mH_dCl_eF_f$ compound(s) ordinarily should be at least about 1:1. Typically, the molar ratio of hydrogen to said compounds of the formula $C_mH_dCl_eF_f$ ranges from about 1:1 to about 5:1, preferably from about 1:1 to 3:1, and more preferably from about 1:1 to 2:1. In general, with a given catalyst composition, the higher the temperature and the longer the contact time, the greater is the conversion to dehalogenated products. The above variables can be balanced, one against the other, so that the formation of dehalogenated products is maximized.

Examples of halogenated hydrocarbons of the formula $C_mH_dCl_cF_f$ which may be reacted with hydrogen include $CCl_2FCClF_2$, $CClF_2CCl_2CF_3$, $CClF_2CClFCClF_2$, $CClF_2CF_2CClF_2$, $CClF_2CClFCF_3$ and $CCl_2FCF_2CF_3$. Of note is a catalytic process for producing 1,1,3,3,3-pentafluoropropene-1 (i.e., F1225zc or $CF_2$=$CHCF_3$) by the reaction of hydrogen with $CClF_2CHClCF_3$. This dehalogenation reaction is done in the presence of the catalysts of the instant invention and is preferably conducted at about 125° C. to 325° C., more preferably about 150° C. to 275° C.

Also of note is a catalytic process for producing hexafluoropropene (i.e., HFP or $CF_2$=$CFCF_3$). The starting material is 1,2-dichloro-1,1,2,3,3,3-hexafluoropropane. A catalytic process for producing 1-chloro-1,2,2-trifluoroethene (i.e., CTFE or $CClF$=$CF_2$) from 1,1,2-trichloro-1,2,2-trifluoroethane is also of note.

In another embodiment of this invention isomer mixtures can be reacted using the catalysts of this invention to afford products resulting from dimerization of one isomer and dehalogenation of the other isomer. For example, a mixture of $CCl_3CF_3$ and $CCl_2FCClF_2$ (i.e., $C_2Cl_3F_3$ isomers) can be reacted with hydrogen in the presence of the catalysts of the instant invention at from about 100° C. to 300° C., preferably at from about 125° C. to 275° C., and more preferably at from about 150° C. to about 250° C., with a contact time of from about 1 to about 100 seconds, preferably from about 5 to about 60 seconds. The ratio of hydrogen to the $C_2Cl_3F_3$ isomers ordinarily should be at least about 0.5:1. Typically, the molar ratio of hydrogen to the $C_2Cl_3F_3$ isomers is within the range of from about 0.5:1 to about 10:1, preferably from about 0.5:1 to 5:1, and more preferably from about 0.5:1 to 2:1. The product of the reaction contains $CF_3CCl$=$CClCF_3$ from $CCl_3CF_3$ dimerization and $CClF$=$CF_2$ from $CCl_2FCClF_2$ dehalogenation. If a mixture of $C_2Cl_3F_3$ isomers which contains less than about 10% of the $CCl_3CF_3$ (CFC-113a) isomer is reacted in the same manner at temperatures at or below about 150° C., then CFC-113a is predominantly dimerized to $CF_3CCl$=$CClCF_3$ and small amounts of other hydrogenated products. Very little of the $CCl_2FCClF_2$ (CFC-1 13) isomer is dehalogenated to CTFE. This procedure can be used to obtain pure CFC-113. In the same manner a mixture of $CCl_3CClF_2$ and $CCl_2FCCl_2F$ can be reacted to obtain $CClF_2CCl$=$CClCClF_2$ from $CCl_3CClF_2$ and $CClF$=$CClF$ from $CCl_2FCCl_2F$.

Homogeneously dispersed multiphase catalysts of ruthenium and fluorides of at least one element selected from the group consisting of Al, Co, Cr, Fe, V, Sc and Ga may be used in accordance with this invention in a process for increasing the fluorine content of compounds having the formula $C_jH_gCl_hF_i$, by reacting the compounds with HF in the vapor phase in the presence of the homogeneously dispersed multiphase catalysts. Suitable catalysts for this reaction include compositions consisting essentially of fluorides of at least one element selected from the above disclosed group homogeneously dispersed with ruthenium. Preferred catalysts are homogeneously dispersed ruthenium with $CrF_3$ or with beta-$AlF_3$.

The reaction of said compounds of the formula $C_jH_gCl_hF_i$ with HF in the presence of the catalysts of the instant invention is typically conducted at a temperature from about 150° C. to 400° C., preferably from about 150° C. to 375° C., and more preferably from about 175° C. to about 350° C. Typically the contact time is from about 1 to about 120 seconds, preferably from about 5 to about 60 seconds. The amount of HF ordinarily should be at least a stoichiometric amount. Typically, the molar ratio of HF to said compounds of the formula $C_jH_gCl_hF_i$ ranges from about 1:1 to about 20:1, preferably from about 2:1 to 10: 1, and more preferably from about 3:1 to 6:1. In general, with a given catalyst composition, the higher the temperature and the longer the contact time, the greater is the conversion to fluorinated products. The above variables can be balanced, one against the other, so that the formation of higher fluorine substituted products is maximized.

Examples of saturated compounds which may be reacted with HF include $CH_2Cl_2$ and $CCl_3CF_3$. Of note is a catalytic process for producing difluoromethane (i.e., HFC-32 or $CH_2F_2$) by the fluorination of $CH_2Cl_2$. HFC-32 is produced by reacting $CH_2Cl_2$ with HF in the vapor phase in the presence of the catalysts of this invention. The reaction of $CH_2Cl_2$ with HF in the presence of the catalysts of the instant invention is preferably conducted at about 150° C. to 350° C., more preferably about 175° C. to 250° C. Oxygen may be added, if desired.

Also of note is a catalytic process for producing 2,2-dichloro-1,1,1,2-tetrafluoroethane ($CCl_2FCF_3$, i.e., CFC-114a) by the fluorination of $CCl_3CF_3$.

Homogeneously dispersed multiphase catalysts of ruthenium and fluorides of at least one element selected from the group consisting of Al, Co, Cr, Fe, V, Sc and Ga may be used in accordance with this invention in a process for hydrodechlorinating compounds having the formula $C_kH_pCl_qF_r$, by contacting the saturated compounds with the homogeneously dispersed multiphase catalysts in the presence of hydrogen in the vapor phase. Suitable catalysts for this reaction include compositions consisting essentially of fluorides of at least one element selected from the above disclosed group homogeneously dispersed with ruthenium.

The reaction of said compounds of the formula $C_kH_pCl_qF_r$ with hydrogen is conducted in the presence of the catalysts of the instant invention. The reaction is typically conducted at a temperature from about 100° C. to 350° C., preferably from about 125° C. to 300° C., and more preferably from about 150° C. to about 250° C. Typically the contact time is from about 1 to about 100 seconds, preferably about 5 to about 60 seconds. Typically, the molar ratio of hydrogen to the said compounds of the formula $C_kH_pCl_qF_r$ can range from about 1:1 to about 10:1, preferably about 1:1 to 5: 1, and more preferably about 1:1 to 4:1.

Examples of saturated compounds which may be reacted with hydrogen include $CCl_2FCF_3$ and $CHCl_2CF_3$. Of note is a catalytic process for producing 2-chloro-1,1,1,2-tetrafluoroethane (i.e., $CHClFCF_3$ or HCFC-124) by the hydrogenolysis of $CCl_2FCF_3$. HCFC-124 is produced by reacting $CCl_2FCF_3$ with hydrogen in the vapor phase in the presence of the catalysts of this invention. The reaction of $CCl_2FCF_3$ with hydrogen in the presence of the catalysts of the instant invention is preferably conducted at about 125° C. to 300° C., more preferably about 150° C. to 250° C.

Also of note is a catalytic process for producing 2-chloro-1,1,1-trifluoroethane (i.e., $CH_2ClCF_3$ or HCFC-133a) and 1,1,1-trifluoroethane (i.e., $CH_3CF_3$ or HFC-143a) by reacting $CHCl_2CF_3$ with hydrogen in the vapor phase in the presence of the catalysts of this invention. The reaction of $CHCl_2CF_3$ with hydrogen in the presence of the catalysts of the instant invention is preferably conducted at about 125° C. to 300° C., more preferably about 150° C. to 250° C.

The processes for dimerizing, dehalogenating, dehydrohalogenating, hydrofluorinating and hydrodehalogenating halogenated hydrocarbons in accordance with this invention may be conducted in any suitable reactor, including fixed and fluidized bed reactors. The reaction vessel should be constructed from materials which are resistant to the corrosive effects of hydrogen fluoride and hydrogen chloride such as Inconel™ nickel alloy and Hastelloy™ nickel alloy.

Atmospheric and superatmospheric pressures are the most convenient and are therefore preferred. The reaction products may be separated by conventional techniques such as distillation. It is noted that many halogenated hydrocarbon products of the above reactions form azeotropes with HF, HCl, or other halogenated hydrocarbons.

Without further elaboration, it is believed that one skilled in the art can, using the description herein, utilize the present invention to its fullest extent. The following preferred specific embodiments are, therefore, to be construed as merely illustrative, and does not constrain the remainder of the disclosure in any way whatsoever.

EXAMPLES 1–6c

Examples 1–6c were carried out using essentially the same procedure.

To make a composition having the formula $(NH_3)_6RuMF_6$, stoichiometric quantities of $(NH_3)_6RuCl_3$ and the M metal trichlorides (or an oxide when M=Ga, V) were weighed separately into a Teflon® (polytetrafluoroethylene) beaker. The specific quantities used in the examples are shown in Table I. The $(NH_3)_6RuCl_3$ was dissolved in 20 mL of deionized water and 20 mL of 48 % aqueous HF (Solution A). The M metal trichlorides were dissolved separately in 10 mL of deionized water (Solution B). For the preparation of $(NH_3)_6RuVF_6$ and $(NH_3)_6RuGaF_6$ phases, $V_2O_3$ and $Ga_2O_3$ were used as starting materials and were dissolved in a mixture containing 5 mL of deionized $H_2O$ and 5 mL of 48% aqueous HF (Solution B). Solution B was added to solution A under constant stirring conditions. The precipitate which formed was filtered and washed with deionized water and dried at about 110° C. for about 12 hours.

TABLE I

| Example | Compound | M cation source | $(NH_3)_6RuCl_3$ |
|---|---|---|---|
| 1 | $(NH_3)_6RuAlF_6$ | $AlCl_3 \cdot 6H_2O$ 2.4150 g | 3.0960 g |
| 2 | $(NH_3)_6RuScF_6$ | $ScCl_3 \cdot 6H_2O$ 2.5942 g | 3.0960 g |
| 3 | $(NH_3)_6RuVF_6$ | $V_2O_3$ 0.3748 g | 1.5480 g |
| 4 | $(NH_3)_6RuCrF_6$ | $CrCl_3 \cdot 6H_2O$ 2.6645 g | 3.0960 |
| 5 | $(NH_3)_6RuGaF_6$ | $Ga_2O_3$ 0.2343 g | 0.7740 g |
| 6 | $(NH_3)_6RuFeF_6$ | $FeCl_3$ 1.6230 g | 3.0960 g |

$(NH_3)_6Ru_{1-x}Co_xAlF_6$ compositions were prepared in a similar manner as that used for $(NH_3)_6RuMF_6$ compositions. The compositions that were prepared are shown in Table IA.

TABLE 1A

| Example | Compound | $(NH_3)_6RuCl_3$ | $(NH_3)_6CoCl_3$ | $AlCl_3 \cdot 6H_2O$ |
|---|---|---|---|---|
| 6a | $(NH_3)_6Ru_{0.2}Co_{0.8}AlF_6$ | 2.4770 g | 2.4143 g | 0.5350 g |
| 6b | $(NH_3)_6Ru_{0.5}Co_{0.5}AlF_6$ | 1.5481 g | 2.4143 g | 2.1398 g |
| 6c | $(NH_3)_6Ru_{0.8}Co_{0.2}AlF_6$ | 0.6192 g | 2.4143 g | 1.3374 g |

Powder X-ray diffraction patterns of the phases showed the formation of single phase products and could be indexed on the basis of a cubic unit cell (space group: Pa3). The lattice parameters, determined by indexing the observed x-ray diffraction data, are given in Table II. Infrared and Raman spectra of the phases showed the presence of hexaammine groups and the microprobe analysis of four of the representative phases showed the Ru:M:F ratio to be 1:1:6.

TABLE II

| Example | Composition | Lattice parameter a, ±0.001 Å (±.0001 nm) |
|---|---|---|
| 1 | $(NH_3)_6RuAlF_6$ | 9.987 (.9987) |
| 2 | $(NH_3)_6RuScF_6$ | 10.239 (1.0239) |
| 3 | $(NH_3)_6RuVF_6$ | 10.125 (1.0125) |
| 4 | $(NH_3)_6RuCrF_6$ | 10.090 (1.0090) |
| 5 | $(NH_3)_6RuGaF_6$ | 10.096 (1.0096) |
| 6 | $(NH_3)_6RuFeF_6$ | 10.128 (1.0128) |
| 6a | $(NH_3)_6Ru_{0.8}Co_{0.2}AlF_6$ | 9.962 (0.9962) |
| 6b | $(NH_3)_6Ru_{0.5}Co_{0.5}AlF_6$ | 9.940 (0.9940) |
| 6c | $(NH_3)_6Ru_{0.2}Co_{0.8}AlF_6$ | 9.900 (0.9900) |

Thermogravimetric analysis of each of the product, between room temperature and 600° C., in nitrogen, showed the compounds to undergo decomposition between about 300° C. and 400° C., the weight loss corresponding to the formation of Ru metal and metal tri- or di-fluorides.

The compositions (Examples 1–6) were heated to about 300° C. to 400° C. for 3 hours in nitrogen and the X-ray of the resulting product showed the presence of essentially metallic ruthenium and metal fluorides (such as $\beta$-$AlF_3$). The results are given in Table III. The products were granulated to form 1.2 to 1.7 mm particles for catalyst evaluation.

TABLE III

Decomposition Products of $(NH_3)_6RuMF_6$

| Example | Precursor | Product Catalyst |
|---|---|---|
| 1 | $(NH_3)_6RuAlF_6$ | Ru + $\beta$-$AlF_3$ |
| 2 | $(NH_3)_6RuScF_6$ | Ru + $ScF_3$ |
| 3 | $(NH_3)_6RuVF_6$ | Ru + amorphous fluoride of vanadium |
| 4 | $(NH_3)_6RuCrF_6$ | Ru + $CrF_3$ |
| 5 | $(NH_3)_6RuGaF_6$ | Ru + $\gamma$-$GaF_3$ |
| 6 | $(NH_3)_6RuFeF_6$ | Ru + $FeF_2$ |

General Procedure for Examples 7–24

For most of the experiments, the granulated catalyst was placed in a 5/8" (1.58 cm) Inconel™ nickel alloy reactor heated in a fluidized sand bath. It was heated to about 200° C. in a flow of nitrogen (50 cc/min) for about two hours. After this period, it was heated in a stream of hydrogen (50 cc/min) for about 2 hours at 200° C. prior to evaluation. Liquid feeds were delivered using a metering pump and were vaporized and mixed with either HF or hydrogen prior to entering the reactor. Vapor feeds were delivered using standard mass flow meters.

In some instances, a microreactor was used. It was made of ¼" (0.64 cm) tubing of Hastelloy™ nickel alloy. The catalyst was charged into this reactor to a height of about 5.7 cm. Except where otherwise indicated, the amount of catalyst was 1.24 g in the case of Ru/$\beta$-$AlF_3$, 0.82 g in the case of Ru/$CrF_3$ and 0.70 g in the case of amorphous fluoride of vanadium. They were supported in the bottom by an Incone™ nickel alloy screen. Drying and reduction of these catalysts were done in the larger reactor above and the treated catalysts transferred to the microreactor for evaluation. Substrates to be evaluated were loaded into a Fisher-Porter® pressure tube maintained at about 25° C. Hydrogen was bubbled through the organic substrate to provide a vapor stream of the organic and hydrogen which was sent through the catalyst bed maintained at the desired temperature.

General Procedure for Product Analysis

The following general procedure is illustrative of the method used for both reactors. Part of the total reactor effluent was sampled on-line for organic product analysis using a Hewlett Packard HP 5880 or 5890 gas chromatograph equipped with a 20' (6.1 m) long×⅛" (0.32 cm) diameter tubing containing Krytox™ perfluorinated polyether on an inert carbon support. The helium flow was 35 mL/min. Gas chromatographic conditions were 70° C. for an initial hold period of three minutes followed by temperature programming to 180° C. at a rate of 6° C./minute. Unless indicated, the reported results are in mole %. Positive product identification was obtained using mass and infrared spectroscopy.

The bulk of the reactor effluent containing organic products and also inorganic acids such as HCl and HF was treated with aqueous caustic to neutralize the acids prior to disposal.

Legend

F12 is $CF_2Cl_2$
F13 is $CClF_3$
F21 is $CHCl_2F$
F22 is $CHClF_2$
F31 is $CH_2ClF$
F32 is $CH_2F_2$
F112a is $CCl_3CClF_2$
F113 is $CCl_2FCClF_2$
F113a is $CCl_3CF_3$
F123 is $CHCl_2CF_3$
F123a is $CHClFCClF_2$
F133a is $CH_2ClCF_3$
F114 is $CClF_2CClF_2$
F114a is $CCl_2FCF_3$
F124 is $CHClFCF_3$
F124a is $CHF_2CClF_2$
F134 is $CHF_2CHF_2$
F134a is $CH_2FCF_3$
F143a is $CH_3CF_3$
F152a is $CH_3CHF_2$
F215aa is $CClF_2CCl_2CF_3$
F215ba is $CClF_2CClFCClF_2$
F215ca is $CCl_2FCF_2ClF_2$
F215cb is $CCl_3CF_2CF_3$
F225ca is $CHCl_2CF_2CF_3$
F225cb is $CHClFCF_2CClF_2$

Legend

F226da is $CF_3CHClCF_3$
F236fa is $CF_3CH_2CF_3$
F356mff is $CF_3CH_2CH_2CF_3$
HFA is $CF_3COCF_3$
PCE is $CCl_2=CCl_2$
F1112a is $CF_2=CCl_2$
F1113 is $CClF=CF_2$
F1114 is $CF_2=CF_2$
F1214ya is $CCl_2=CFCF_3$
F1215xc is $CF_2=CClCF_3$
F1215yb is $CClF=CFCF_3$
F1225zc is $CF_3CH=CF_2$
F1316mxx is $CF_3CCl=CClCF_3$ (cis/trans isomers)
F1326mxz is $CF_3CH=CClCF_3$ (cis/trans isomers)
F1336mzz is $CF_3CH=CHCF_3$ (cis/trans isomers)
F151-10mcxx is $C_2F_5CCl=CClC_2F_5$ (cis/trans isomers)
F153-10mczz is $C_2F_5CH=CHC_2F_5$ (cis/trans isomers)
F151-12mmtt is $(CF_3)_2C=C(CF_3)_2$

EXAMPLE 7

Ru/β-AlF₃ Catalyst (9.7 g, 10 cc)

The reaction of F113a and hydrogen was studied. The contact time for all runs was 20 seconds, except for the run at 206° C. which was 10 seconds. The molar ratios of H₂:F113a were as shown in the table. Results in area % are shown below. The major product for the reaction was the dimer olefin.

| Temp. ° C. | H₂:F113a | F143a | F356mff | F123 | F113a | t-F1316mxx | c-F1316mxx | Others[a] |
|---|---|---|---|---|---|---|---|---|
| 205 | 4 | 15.8 | 1.2 | 10.3 | 0.0 | 44.5 | 22.0 | 6.2 |
| 206 | 8 | 21.3 | 1.8 | 8.8 | 0.0 | 41.7 | 20.0 | 6.4 |
| 176 | 2 | 10.0 | 0.4 | 14.1 | 1.7 | 48.4 | 23.0 | 2.3 |
| 175 | 2 | 10.3 | 0.5 | 14.4 | 1.7 | 48.1 | 22.7 | 2.3 |
| 175 | 4 | 15.9 | 3.7 | 15.7 | 0.1 | 41.8 | 19.0 | 3.8 |
| 175 | 1 | 3.3 | 0.0 | 9.0 | 18.3 | 45.8 | 22.1 | 1.5 |

[a]Others include CH₄, C₂H₆, F133a, F1336mzz, F114a, F1326mxz, F113, as well as unidentified products -continued Legend F225da is $CClF_2CHClCF_3$
F216aa is $CF_3CCl_2CF_3$
F216a is $CClF_2CClFCF_3$
F216cb is $CCl_2FCF_2CF_3$

EXAMPLE 8

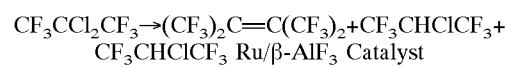

Using the catalyst of Example 7, the reaction of F216aa and hydrogen was studied. The contact time was 20 seconds in all instances and results are reported in area %.

| Temp. ° C. | H₂:F216aa | F1225zc | F236fa | F1215xc | F226da | F216aa | F151-12mmtt | Others[b] |
|---|---|---|---|---|---|---|---|---|
| 175 | 1.0 | 0.6 | 4.9 | 7.5 | 29.6 | 46.8 | 7.9 | 2.7 |
| 200 | 1.0 | 1.6 | 8.6 | 8.1 | 38.5 | 22.7 | 16.9 | 3.5 |
| 200 | 0.5 | 0.3 | 3.9 | 4.5 | 17.1 | 57.4 | 14.1 | 2.5 |
| 250 | 0.5 | 0.2 | 2.7 | 2.4 | 10.0 | 54.8 | 28.4 | 1.7 |
| 300 | 0.5 | 0.0 | 1.1 | 1.8 | 13.4 | 54.0 | 27.8 | 1.9 |

[b]Others include F216ba and F153-10mczz, and small amounts of other unknowns

EXAMPLE 9

Catalyst

Using the catalyst of Example 7, the reaction of hydrogen and F123 was studied. The hydrogen-to-organic ratio was 1/1, the contact time 20 seconds and the reaction temperature 200° C. Results in area % are shown below. The products primarily correspond to those arising from the replacement of chlorine by hydrogen.

| $CH_4$ | $C_2H_6$ | F143a | F133a | F1336mzz | F123 | Others |
|---|---|---|---|---|---|---|
| 1.1 | 1.1 | 30.8 | 21.2 | 0.3 | 44.0 | 1.6 |
| 0.7 | 0.8 | 24.2 | 20.9 | 0.3 | 51.4 | 1.7 |

EXAMPLE 10

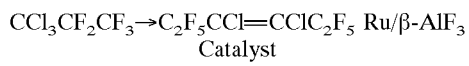
Catalyst

Using the catalyst of Example 7, the reaction of F215cb and hydrogen was studied. The hydrogen-to-organic ratio was 1/1 and the contact time was 30 seconds. The results are reported in area %. The starting feed contained 3.3 % F215aa, 95.8% F215cb and small quantities of other products. The major product of the reaction was olefinic dimer.

| Temp. ° C. | F225ca | F215aa | F215cb | F151-10 mcxx | F151-10 mcxx | Others |
|---|---|---|---|---|---|---|
| 175 | 2.6 | 0.0 | 2.4 | 82.1 | 10.3 | 1.2 |
| 176 | 2.1 | 0.1 | 2.5 | 82.6 | 10.7 | 1.1 |
| 150 | 1.8 | 0.5 | 3.5 | 83.8 | 9.5 | 0.6 |

EXAMPLE 11

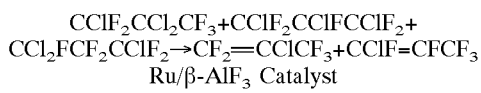
Ru/β-AlF₃ Catalyst

Using the catalyst of Example 7, the reaction of a mixture of F215 and hydrogen was studied. The contact time was 20 seconds in all cases. The molar ratios of $H_2$:F215 mixtures were 1:1 except for the second 175° C. run where it was 2:1. The feed to the reactor analyzed for 25.5% F215aa, 63% F215ba and 11.4% F215ca in addition to small amounts of other products. The results reported are in area %. The primary products of the reaction are the uncoupled olefins.

| Temp. ° C. | F1215xc | F1215yb | F225 cb + ca | F215aa | F215ba | F215ca | Others |
|---|---|---|---|---|---|---|---|
| 150 | 40.8 | 5.6 | 0.4 | 0.4 | 40.2 | 9.5 | 2.9 |
| 175 | 46.4 | 8.1 | 0.5 | 0.1 | 32.6 | 9.3 | 3.0 |
| 175 | 49.4 | 9.6 | 0.7 | 0.0 | 27.5 | 9.1 | 3.7 |
| 200 | 50.3 | 10.1 | 1.0 | 0.0 | 26.4 | 8.7 | 3.5 |
| 250 | 58.2 | 15.1 | 7.3 | 0.0 | 12.2 | 1.5 | 5.7 |
| 275 | 59.9 | 16.6 | 8.1 | 0.0 | 8.8 | 0.6 | 6.0 |

EXAMPLE 12

AlF₃ Catalyst

Using the catalyst of Example 7, the reaction of hydrogen and HF with F113a was studied. The molar ratio of HF:$H_2$:F113a was 2:1:1 for the 15 second contact time (C.T.) runs and was 2:0:1 for the 30 second contact time runs. The reaction temperature was 275° C. and the results reported below are in area %.

| C.T. Sec. | F143a | F114a | F123 | F113a | t-F1316 mxx | c-F1316 mxx | Others[c] |
|---|---|---|---|---|---|---|---|
| 15 | 1.5 | 1.1 | 16.1 | 2.5 | 46.9 | 28.1 | 3.8 |
| 15 | 0.8 | 0.9 | 9.6 | 15.3 | 44.1 | 26.4 | 2.9 |
| 30 | 0.0 | 1.3 | 0.2 | 96.6 | 0.7 | 0.5 | 0.8 |
| 30 | 0.0 | 1.5 | 0.0 | 97.2 | 0.4 | 0.3 | 0.6 |

[c] Others include F113, F133a, PCE, F1326mxz, and minor quantities of other unknowns

EXAMPLE 13

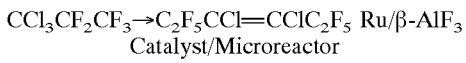
Catalyst/Microreactor

Hydrogen (10 sccm, i.e., 1.67×10⁻⁷ m³/s) was bubbled through liquid F215cb at about 25° C. and the gas mixture sent through the catalyst at 200° C. The major product observed was $CF_3$-$CF_2$-CCl=CCl-$CF_2$-$CF_3$ ($C_6F_{10}Cl_2$, F151-10 mcxx, 75%). The cis and trans isomers of this compound were present in about a 10:65 ratio. The results are reported in area %.

EXAMPLE 14

Catalyst/Microreactor

Example 13 was repeated except that the organic feed was F225da. Product analysis indicated about 20 area % F1225zc, and about 2% unknowns, the remaining being starting material.

EXAMPLE 15

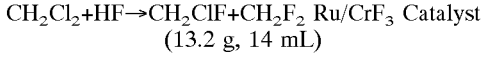
(13.2 g, 14 mL)

The reactor was charged with the catalyst and dried in a stream of nitrogen at 200° C. for about 2 hours prior to use. The reactor was operated at 200° C. with an HF-to-organic ratio of 4/1 and a contact time of 15 seconds. Product analysis indicated the following.

| F32 | F22 | F31 | F21 | $CH_2Cl_2$ | $CHCl_3$ | Others |
|---|---|---|---|---|---|---|
| 24.5 | 0.8 | 15.8 | 1.5 | 56.0 | 1.4 | 0.0 |
| 26.7 | 0.3 | 15.1 | 0.4 | 57.2 | 0.4 | 0.0 |
| 28.1 | 0.1 | 14.6 | 0.2 | 56.9 | 0.1 | 0.0 |
| 29.8 | 0.1 | 14.6 | 0.1 | 55.3 | 0.1 | 0.0 |
| 31.9 | 0.1 | 14.4 | 0.1 | 53.5 | 0.1 | 0.0 |

| Temp., °C. | Catalyst | HFP | F1215yb | F216ba | Unknowns |
|---|---|---|---|---|---|
| 200 | A | 6.6 | 0.0 | 92.9 | 0.5 |
| 250 | A | 22.9 | 0.0 | 76.4 | 0.4 |
| 300 | A | 41.9 | 0.0 | 55.3 | 2.8 |
| 200 | B | 5.7 | 1.2 | 90.4 | 2.7 |

EXAMPLE 16

$CCl_3CF_3 + HF \rightarrow CCl_2FCF_3$ Ru/$CrF_3$ Catalyst (13.2 g, 14 mL)

Using the catalyst of Example 13, the fluorination of F113a was carried out. The HF-to-F113a ratio was 2:1, and the contact time was 15 seconds. The following results were obtained.

| Temp., °C. | F13 | F114a | F1112a | F113a |
|---|---|---|---|---|
| 250 | 0.1 | 14.8 | 0.2 | 84.8 |
| 275 | 0.1 | 31.3 | 0.6 | 67.9 |
| 300 | 0.1 | 63.4 | 1.0 | 35.4 |

EXAMPLE 17

$CCl_3CF_2CF_3 \rightarrow C_2F_5CCl=CClC_2F_5 + CCl_2=CFCF_3$ Ru/$CrF_3$ Catalyst/Microreactor Example 13 was substantially repeated except that the catalyst was Ru/$CrF_3$. In addition to cis/trans F151-10mcxx (75 area %), about 22 area % 1214ya was also observed.

EXAMPLE 18

$CClF_2CHClCF_3 \rightarrow CF_3CH=CF_2$ Ru/$CrF_3$ Catalyst/Microreactor

Example 14 was substantially repeated except that the catalyst was Ru/$CrF_3$. Area % product analysis indicated about 16% F1225zc, and about 2% unknowns, the remaining being starting material.

EXAMPLE 19

$CClF_2CClFCF_3 \rightarrow CF_2=CFCF_3$ Ru/$\beta$-$AlF_3$ (A) or Ru/$CrF_3$ (B) Catalyst/Microreactor Hydrogen (10 sccm, i.e., $1.67 \times 10^{-7}$ m$^3$/s) was bubbled through liquid F216ba maintained at about 25° C. The vapor mixture was passed through the catalysts maintained in independent microreactors. The major olefinic product was hexafluoropropylene (HFP, $CF_3CF=CF_2$). Average product analysis from the two catalysts in area % is shown below.

EXAMPLE 20

$CCl_2FCClF_2 \rightarrow CClF=CF_2$ Ru/$CrF_3$ Catalyst/Microreactor

Hydrogen, 1.5 sccm ($2.5 \times 10^{-8}$ m$^3$/s), was bubbled through F113 maintained at about 25° C. and the mixture sent through the catalyst bed at 200° C. Area % product analysis indicated 13.3% chlorotrifluoroethylene (CTFE, $CClF=CF_2$), 5.5% F123a and 4% F123 in addition to unconverted starting material, and small quantities of other products.

EXAMPLE 21

$CCl_3CF_3 \rightarrow CF_3CCl=CClCF_3 + CHCl_2CF_3$ Ru/$FeF_2$ Catalyst (7.7 g, 5 mL)

The reactor was charged with Ru/$FeF_2$ dried in a stream of nitrogen and reduced in a stream of hydrogen according to the general procedure prior to use. The reactor was operated at 175 °C. with a hydrogen:F113a ratio of 1:1 and at a contact time of 20 seconds. The results are reported in area %.

| F143a | F114a | F123 | F113a | t-F1316 mxx | c-F1316 mxx | Others |
|---|---|---|---|---|---|---|
| 1.3 | 0.6 | 15.3 | 5.6 | 50.2 | 25.7 | 1.3 |
| 1.0 | 0.6 | 13.2 | 9.0 | 49.6 | 25.7 | 1.0 |
| 0.9 | 0.6 | 12.3 | 10.7 | 49.1 | 25.6 | 0.9 |

EXAMPLE 22

$CCl_2FCF_3 \rightarrow CHClFCF_3$ Ru/$FeF_2$ Catalyst (7.7 g, 5 mL)

Using the catalyst of Example 19, the reaction of hydrogen and F114a was carried out. The hydrogen-to-organic ratio was 2:1 and the contact time 20 seconds.

| Temp., °C. | CH₄ | C₂H₆ | F143a | F134a | F124 | F133a | F114a | F123 | Others |
|---|---|---|---|---|---|---|---|---|---|
| 175 | 0.4 | 0.4 | 1.0 | 0.1 | 10.1 | 0.6 | 85.6 | 1.2 | 0.7 |
| 200 | 1.4 | 0.8 | 1.5 | 0.2 | 24.1 | 0.5 | 70.2 | 0.6 | 0.7 |
| 225 | 3.7 | 1.4 | 2.8 | 0.6 | 41.4 | 0.7 | 47.6 | 0.5 | 1.3 |

EXAMPLE 23

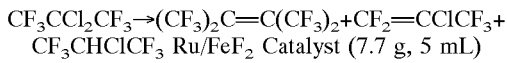

Ru/FeF₂ Catalyst (7.7 g, 5 mL)

Using the catalyst of Example 19, the reaction of hydrogen and F216aa was carried out at a contact time of 20 seconds. The reported results are in area %.

| Temp. °C. | H₂: 216aa | F1215xc | F226da | F216aa | C₆F₁₀ | C₆HF₁₁ | F151-12mmtt | Others |
|---|---|---|---|---|---|---|---|---|
| 200 | 2.0 | 38.2 | 21.8 | 20.8 | 1.1 | 1.0 | 15.1 | 2.0 |
| 200 | 1.0 | 25.7 | 14.4 | 39.8 | 1.0 | 1.0 | 16.4 | 1.6 |
| 200 | 0.5 | 16.3 | 8.4 | 58.1 | 0.8 | 0.7 | 14.3 | 1.4 |
| 250 | 0.5 | 19.9 | 7.7 | 52.0 | 0.5 | 0.3 | 18.1 | 1.6 |
| 300 | 0.5 | 15.2 | 12.9 | 55.6 | 0.3 | 0.2 | 13.8 | 2.2 |

Compounds of the formulas C₆F₁₀ and C₆F₁₁H were determined by mass spectrometry.

EXAMPLE 24

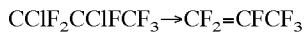

Ru/Amorphous Vanadium Fluoride Catalyst/ Microreactor

Example 17 was substantially repeated at 200° C., except that ruthenium/amorphous vanadium fluoride catalyst was used. Area % product analysis indicated 36.7% HFP and 58.5% starting material, the remaining being unknowns.

EXAMPLE 25

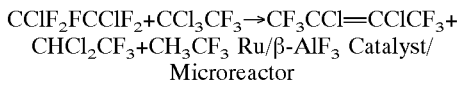

Ru/β-AlF₃ Catalyst/ Microreactor

Through the microreactor, maintained at 150° C. and containing 0.54 g catalyst, was passed a vapor stream containing 90.3% F113 and 8.8% F113a and hydrogen, obtained by bubbling hydrogen through the liquid mixture maintained at 25° C. The total organic and hydrogen feed rate to the reactor was 10 cc/min. Product analysis in area % indicated 1.4% F143a, 2.6% CTFE, 2.3% F123, 85.8% F113, 4.5% of a cis/trans mixture of F1316mxx and small quantities of other products.

What is claimed is:

1. A process for decreasing the chlorine to carbon ratio for halogenated hydrocarbons containing chlorine and from 1 to 6 carbon atoms, in the presence of a multiphase catalyst, characterized by:

(1) preparing a single phase solid catalyst precursor which has a structure that collapses at a temperature of about 400° C. or less and has the formula $(NH_3)_6Ru_{1-r-s}Co_rCr_sMF_6$, where r+s is in the range of 0.00 to 0.99, and M is at least one trivalent metal selected from the group consisting of Al, Cr, Fe, V, Sc and Ga; and (2) producing said multiphase catalyst by heating said single phase solid catalyst precursor to about 400° C. or less in a non-oxidizing atmosphere to produce a multiphase composition wherein a phase containing ruthenium is homogeneously dispersed with a phase containing metal fluoride.

2. The process of claim 1 wherein two chlorine substituents are removed from a compound having the formula $C_nH_aCl_bF_c$ where n is an integer from 1 to 4, a is an integer from 0 to 1, b is an integer from 2 to 9, c is an integer from 0 to 9, where a+b+c equals 2n+2, and where two chlorines that are removed are on the same carbon atom, and the compound is dimerized by reacting said compound with hydrogen in the vapor phase to produce an olefin of the formula $C_{2n}H_{2a}Cl_{2b-4}F_{2c}$.

3. The process of claim 1 wherein a saturated compound having the formula $C_mH_dCl_eF_f$ where m is an integer from 2 to 6, d is an integer from 0 to 2, e is an integer from 2 to 4, f is an integer from 3 to 12, where d+e+f equals 2m+2, is dehalogenated by reacting said compound with hydrogen in the vapor phase to produce an olefin of the formula $C_mH_dCl_{e-y}F_{f-y}$, where y is an integer from 1 to 2 when m is an integer from 2 to 3, and y is an integer from 2 to 4 when m is an integer from 4 to 6, provided that a chlorine atom on each of two adjacent carbons or a fluorine and a chlorine atom on two adjacent carbons, but not a fluorine atom on each of two adjacent carbons are removed.

4. The process of claim 3 wherein CClF₂CHClCF₃ is reacted with hydrogen to produce CF₂=CHCF₃.

5. The process of claim 3 wherein CF₃CFClCF₂Cl is reacted with hydrogen to produce CF₃CF=CF₂.

6. The process of claim 1 wherein the fluorine content of either a saturated compound or an unsaturated olefinic compound having the formula $C_jH_gCl_hF_i$ where j is an integer from 1 to 6, g is an integer from 0 to 4, h is an integer from 1 to 13, i is an integer from 0 to 13, provided that h is at least 1 when the compound is saturated, is increased by reacting said compound with HF in the vapor phase.

7. The process of claim 1 wherein a cyclic or acyclic compounds having the formula $C_kH_pCl_qF_t$ where k is an integer from 1 to 6, p is an integer from 0 to 12, q and t are integers from 1 to 13, where p+q+t equals 2k+2, when the compound is saturated and acyclic, equals 2k when the compound is saturated and cyclic or is olefinic and acyclic, and equals 2k-2 when the compound is olefinic and cyclic, is hydrodehalogenated by reacting said compound with hydrogen in the vapor phase.

8. A single phase fluoride composition of the formula $(NH_3)_6Ru_{1-r-s}Co_rCr_sMF_6$, where r+s is in the range of 0.00 to 0.99, and M is at least one trivalent element selected from the group consisting of Al, Cr, Fe, V, Sc and Ga.

9. A multiphase catalyst composition consisting essentially of metallic ruthenium and fluorides of at least one element selected from the group consisting of Al, Co, Cr, Fe, V, Sc and Ga, wherein said ruthenium is homogeneously dispersed with phases of said fluorides.

10. The multiple catalyst composition of claim 9 produced by the process of (1) preparing a single phase solid catalyst precursor which has a structure that collapses at a temperature of about 400° C. or less and has the formula $(NH_3)_6Ru_{1-r-s}Co_rCr_sMF_6$, where r+s is in the range of 0.00 to 0.99, and M is at least one trivalent element selected from the group consisting of Al, Cr, Fe, V, Sc and Ga, and (2) producing said multiphase catalyst by heating said single phase solid catalyst precursor to about 400° C. or less in an non-oxidizing atomsphere to produce a multiphase composition wherein a phase containing ruthenium is homogeneously dispersed with a phase containing metal fluoride.

11. A single phase fluoride composition of claim 8 having the formula $(NH_3)_6RuAlF_6$.

12. A single phase fluoride composition of claim 8 having the formula $(NH_3)_6RuScF_6$.

13. A single phase fluoride composition of claim 8 having the formula $(NH_3)_6RuVF_6$.

14. A single phase fluoride composition of claim 8 having the formula $(NH_3)_6RuCrF_6$.

15. A single phase fluoride composition of claim 8 having the formula $(NH_3)_6RuGaF_6$.

16. A single phase fluoride composition of claim 8 having the formula $(NH_3)_6RuFeF_6$.

17. A single phase fluoride composition of claim 8 having the formula $(NH_3)_6Ru_{0.8}Co_{0.2}AlF_6$.

18. A single phase fluoride composition of claim 8 having the formula $(NH_3)_6Ru_{0.5}Co_{0.5}AlF_6$.

19. A multiphase catalyst composition of claim 9 consisting essentially of metallic ruthenium and fluorides of Al.

20. A multiphase catalyst composition of claim 9 consisting essentially of metallic ruthenium and fluorides of Cr.

* * * * *